(12) United States Patent
Hermonat et al.

(10) Patent No.: US 6,884,605 B2
(45) Date of Patent: Apr. 26, 2005

(54) COMPOSITIONS, METHODS AND PRODUCTS COMPRISING HUMAN PAPILLOMAVIRUS FOR DETECTING AND TREATING A CANCER

(75) Inventors: Paul L. Hermonat, Little Rock, AR (US); V. Suzanne Klimberg, Little Rock, AR (US); Yong Liu, Little Rock, AR (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 139 days.

(21) Appl. No.: 09/927,585

(22) Filed: Aug. 9, 2001

(65) Prior Publication Data

US 2003/0029461 A1 Feb. 13, 2003

(51) Int. Cl.[7] .................................................. C12P 19/34
(52) U.S. Cl. ........................ 435/91.1; 435/6; 536/24.33
(58) Field of Search ................................ 435/91.1, 91.2, 435/6; 536/24.33

(56) References Cited

FOREIGN PATENT DOCUMENTS

JP          5192200      *   8/1993

* cited by examiner

*Primary Examiner*—Ali R. Salimi
(74) *Attorney, Agent, or Firm*—J. M. Gilbreth; Mary A. Gilbrath; Gilbrath & Associates, P.C.

(57) ABSTRACT

Methods for screening a patient for a cancer wherein the methods comprise detecting an HPV in a biopsy from a patient are disclosed. Also disclosed are compositions and products for screening and for treating cancer in a patient, as well as methods of treating a patient afflicted with a cancer.

5 Claims, 12 Drawing Sheets

| Mabs | DC | DC lysate | DC GST-E6 | DC AAV/E6/Neo |
|---|---|---|---|---|
| CD14 | -/- | -/- | -/- | -/- |
| HLA-DR | ++/- | +++/- | +++/- | +++/- |
| CD40 | ++/- | ++/- | ++/- | ++/- |
| CD80 | ++/- | ++/- | ++/- | +++/- |
| CD83 | ++/- | ++/- | ++/- | ++/- |
| CD86 | ++/- | ++/- | +++/- | ++/- |

FIG. 15

DC only lysate-DC

GST-E6
lipof-DC

AAV/E6//Neo
-DC

DC only lysate-DC

GST-E6 lipof-DC

AAV/E6//Neo-DC

SEQUENCE LISTING

<160> NUMBER OF SEQ ID NOS: 10

<210> SEQ ID NO 1
<211> LENGTH: 20
<212> TYPE: DNA
<213> ORGANISM: Artificial Sequence

```
<220> FEATURE:
<223> OTHER INFORMATION: Based on HPV E6 sequence

<400> SEQUENCE: 1
tgtcaaaaac cgttgtgtcc                                                   20

<210> SEQ ID NO 2
<211> LENGTH: 20
<212> TYPE: DNA
<213> ORGANISM: Artificial Sequence
<220> FEATURE:
<223> OTHER INFORMATION: Based on HPV E7 sequence

<400> SEQUENCE: 2
tgctaattcg gtgctacctg                                                   20

<210> SEQ ID NO 3
<211> LENGTH: 20
<212> TYPE: DNA
<213> ORGANISM: Artificial Sequence
<220> FEATURE:
<223> OTHER INFORMATION: Based on HPV-L1 sequence; m=a or c; r=a or g;
      w=a or t; y=c or t

<400> SEQUENCE: 3
gcmcagggwc ataayaatgg                                                   20

<210> SEQ ID NO 4
<211> LENGTH: 20
<212> TYPE: DNA
<213> ORGANISM: Artificial Sequence
<220> FEATURE:
<223> OTHER INFORMATION: Based on HPV-L1 sequence; m=a or c; r=a or g;
      w=a or t; y=c or t

<400> SEQUENCE: 4
cgtccmarrg gawactgatc                                                   20

<210> SEQ ID NO 5
<211> LENGTH: 19
<212> TYPE: DNA
<213> ORGANISM: Artificial Sequence
<220> FEATURE:
<223> OTHER INFORMATION: Based on plasmid pBR322 sequence

<400> SEQUENCE: 5
atacctgtcc gcctttctc                                                    19

<210> SEQ ID NO 6
<211> LENGTH: 16
<212> TYPE: DNA
<213> ORGANISM: Artificial Sequence
<220> FEATURE:
<223> OTHER INFORMATION: Based on plasmid pBR322 sequence

<400> SEQUENCE: 6
aatctgctgc ttgcaa                                                       16

<210> SEQ ID NO 7
<211> LENGTH: 20
<212> TYPE: DNA
<213> ORGANISM: Artificial Sequence
<220> FEATURE:
<223> OTHER INFORMATION: Based on HPV-16 E6 gene
```

```
<400> SEQUENCE: 7
accacagtta tgcacagagc                                               20

<210> SEQ ID NO 8
<211> LENGTH: 20
<212> TYPE: DNA
<213> ORGANISM: Artificial Sequence
<220> FEATURE:
<223> OTHER INFORMATION: Based on HPV-16 E6 gene

<400> SEQUENCE: 8
aggacacagt ggcttttgac                                               20

<210> SEQ ID NO 9
<211> LENGTH: 20
<212> TYPE: DNA
<213> ORGANISM: Artificial Sequence
<220> FEATURE:
<223> OTHER INFORMATION: Based on transcription factor TFIIB sequence

<400> SEQUENCE: 9
gtgaagatgg cgtctaccag                                               20

<210> SEQ ID NO 10
<211> LENGTH: 20
<212> TYPE: DNA
<213> ORGANISM: Artificial Sequence
<220> FEATURE:
<223> OTHER INFORMATION: Based on transcription factor TFIIB sequence

<400> SEQUENCE: 10
gcctcaattt atagctgtgg                                               20
```

COMPOSITIONS, METHODS AND PRODUCTS COMPRISING HUMAN PAPILLOMAVIRUS FOR DETECTING AND TREATING A CANCER

BACKGROUND OF THE INVENTION

1. Field of the Invention

The present invention relates to products, compositions, methods and apparatus for identification of cancers and pre-cancerous cellular changes. In another aspect, the present invention relates to products, compositions, methods and apparatus for identification of breast cancers or pre-cancerous cellular changes in breast tissues. In even another aspect, the present invention relates to products, compositions, methods and apparatus for treatment of cancers and pre-cancerous cellular changes. In still another aspect, the present invention relates to products, compositions, methods and apparatus for treatment of breast cancer and pre-cancerous cellular changes in breast tissues.

2. Description of the Related Art

Breast cancer is the most common form of cancer in women in the United States. It is estimated that in the year 2000, 182,800 new cases of female invasive breast cancer will be diagnosed, and 40,800 women will die from the disease. All women are at risk for breast cancer, with this risk increasing as a woman ages. Women are generally considered to be at increased risk for developing breast cancer if they have one or more of the following risk factors: a) a family history of breast cancer, b) a previous diagnosis of a malignant breast tumor or other gynecological cancers, c) hormonal factors, or d) not having had any children or having the first child later in their child bearing years. Even so, the majority of all breast cancers occur in women who apparently do not have identifiable risk factors.

Breast cancer cannot currently be prevented. But detecting and treating it at an early stage, when the tumor is small and has not spread beyond the breast, can increase the chances of survival significantly. However, not all breast cancers are currently detected at this early stage. Therefore, screening for breast cancer has become a critical aspect in the overall management of this disease.

The techniques currently used to screen for breast cancer and other breast conditions include monthly breast self examination, mammography, and clinical breast examination. Also, genetic testing can be performed for BRCA1 and BRCA2 genes in women who have a strong family history of breast cancer, since these genes are associated with approximately 5 to 10 percent of breast cancer cases. In spite of this genetic knowledge, the genetic changes involved in the vast majority of breast cancers remains largely undetermined.

Human papillomaviruses (HPV) are strongly linked to cervical and other cancers. Cervical cancer (CX CA) is the second most prevalent female cancer world-wide. HPV 16 DNA is present in 65% of CX CAs, and with the other HPV types, more than 90% of CX CAs contain HPV DNA. The E6 and E7 genes of HPV 16s can cause contact-inhibited cells to lose this phenotype. Furthermore, E6 and E7 interact with the cellular anti-oncogenes RB[105] and p53, respectively, leading to their inactivation. Thus, it is widely regarded that HPV-16 is a central etiologic agent and risk factor in the development of cervical/genital cancer. The E7 protein, and possibly E6 as well, also function as transcriptional transactivators of heterologous genes. HPVs have also been found in oral, penile, and vulvar cancer.

It appears that whatever tissue site HPVs are known to infect, they cause pathology. Usually the pathology is limited to a tissue hyperplasia or papilloma. However, there is a significant risk that this higher than normal active cell growth may become an outright malignancy.

However, as recent studies have indicated, the relationship between HPV infection and breast cancer is controversial.

Hennig et al. (1999) have reported that of women studied in Norway having concomitant advanced genital HPV infection (cervical intraepithelial neoplasia III, "CIN III") in addition to breast cancer, 46% of the breast cancers also contained HPV 16. However, of the control study of eight patients having breast cancer diagnosed before the CIN III lesions, none had HPV positive breast carcinomas. Additionally no cases in the study were positive for HPV 11, 18 or 33.

Yu et al. (1999) report that HPV 33 is associated in pre-malignant and malignant breast lesions in Chinese and Japanese populations, and further suggest that HPV 16 and HPV 18 are not involved in breast hyperplastic lesion, especially breast cancer.

In spite of the advancements in the art, there is a need in the art for improved compositions, methods and products for screening a patient for cancer and/or pre-cancerous cellular changes.

There is another need in the art for improved compositions, products and methods for screening a patient for breast cancer and/or pre-cancerous cellular changes in the breast.

There is even another need in the art for improved compositions, products and methods for treating a patient afflicted with a cancer in any stage of development.

There is still another need in the art for improved compositions, products and methods for treating a patient afflicted with breast cancer and/or a pre-cancerous cellular changes in the breast in any stage of development.

These and other needs in the art will become apparent to those of skill in the art upon review of this specification, including its drawings, claims and appendix.

SUMMARY OF THE INVENTION

It is an object of the present invention to provide compositions, methods and products for screening a patient for cancer and/or pre-cancerous cellular changes.

It is another object of the present invention to provide for compositions, products and methods for screening a patient for breast cancer and pre-cancerous cellular changes in the breast.

It is even another object of the present invention to provide compositions, products and methods for treating a patient afflicted with a cancer and/or pre-cancerous cellular changes in any stage of development It is still another object of the present invention to provide compositions, products and methods for treating a patient afflicted with breast cancer and/or a pre-cancerous cellular changes in the breast in any stage of development.

These and other objects in the art will become apparent to those of skill in the art upon review of this specification, including its drawings, claims and appendix.

According to one embodiment of the present invention there is provided a method of screening a patient for a cancer. The method generally comprises performing an amplification technique on a sample from a biopsy taken from a patient. The sample comprises nucleic acid, and the amplification technique is directed to specific amplification of a portion of a human papillomavirus (HPV) sequence contained therein. The method further includes probing for the presence of an HPV sequence in the amplified sequence using an HPV specific probe.

According to another embodiment of the present invention there is provided a method of screening a patient for a cancer. The method generally comprises contacting cellular material together with an HPV specific probe. The cellular material is generally extracted from a sample, such as a biopsy, taken from a patient. The cellular material may be any purified or non-purified cellular material such as, for example, deoxyribonucleic acid (DNA), ribonucleic acid (RNA), polypeptides, or a combination thereof. The cellular material may be purified, either partially or wholly, using any of the methods well known in the art.

The probe used in the screening methods of the invention may be specific to any HPV selected from the group consisting of HPV18, HPV31, HPV 33, HPV35, HPV45, HPV58. In a preferred embodiment, the screening method further comprises contacting the cellular material with a second HPV specific probe, wherein the first and second HPV are different from one another and are selected from the group consisting of HPV18, HPV31, HPV 33, HPV35, HPV45, HPV58. Alternatively, in another embodiment, the screening method further comprises contacting the cellular material with a second HPV specific probe, wherein the first HPV specific probe is specific to HPV 16 and the second HPV specific probe is specific to at least one HPV selected from the group consisting of HPV18, HPV31, HPV 33, HPV35, HPV45, HPV58.

According to even another embodiment of the present invention there is provided a method of treating a patient. The method generally comprises administering a composition comprising an effective amount of an antisense HPV DNA sequence to a patient. Preferably, the antisense HPV DNA sequence is expressed from a viral expression vector, such as an adeno-associated vector. The HPV may be any member of the HPV family, such as, for example, HPV16, HPV18, HPV31, HPV35, HPV45, HPV58, and any combination thereof.

According to still another embodiment of the present invention there is provided a method of treating a patient. The treatment method generally comprises administering an effective amount of a composition to a patient, wherein the composition comprises an agent that inhibits expression of at least one HPV gene.

According to yet another embodiment of the present invention there is provided a method of treating a patient. The treatment method generally comprises administering an effective amount of a composition to a patient, wherein the composition comprises an agent that specifically inhibits an HPV protein. Examples of HPV proteins to target for inhibition include the HPV16 E6 protein and the HPV16 E7 protein. Inhibition of a protein can be by any of the methods known in the art, such as, targeting with an antibody, inhibition of post-translation modification, inhibition of protein stability and half-life. A preferred agent for use in the treatment method of the present invention is an antibody specific for interaction with an epitope of an HPV protein, such as HPV16 E6 protein or HPV16 E7 protein.

According to even still another embodiment of the present invention there is provided a method of treating a patient. The method comprises transfecting dendritic cells (DCs) into a patient, wherein the dendritic cells have been altered to stably produce an HPV antigen. Preferably, a recombinant retrovirus such as for example an adeno-associated virus (AAV) that has been genetically manipulated to comprise a portion of an HPV antigen-encoding gene is used to infect monocyte precursors which are then induced to differentiate into DCs. Differentiation of monocytes in DCs may be accomplished by treating the monocytes with at least one cytokine.

According to even yet another embodiment of the present invention there is provided for a kit useful for screening a patient for a cancer. Generally the kit comprises a probe that is specific for the detection of an HPV family member. The HPV-specific probe may be a single-stranded oligonucleotide sequence, a double-stranded oligonucleotide sequence, a polypeptide, or any combination thereof. The HPV may be any HPV family member including, HPV16, HPV18, HPV31, HPV35, HPV45, HPV58, and any combination thereof. In a preferred embodiment the HPV is HPV16 or HPV18. The probe may be used on any sample derived from a patient.

These and other embodiments of the present invention will become apparent to those of skill in the art upon review of this specification, including its drawings and claims.

BRIEF DESCRIPTION OF THE DRAWINGS

FIG. 14 is a two-color flow cytometric characterization of primed cell populations.

FIG. 15 is the characterization of DC at day 7 under different conditions.

FIG. 16 provides the characterization of CD80 in pulsed DC.

DETAILED DESCRIPTION OF THE INVENTION

Figure 1:
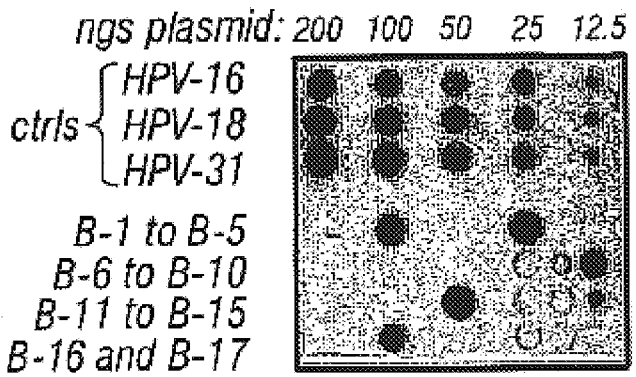
FIG. 1 is a Polymerase Chain Reaction (PCR)/Dot Blot Hybridization analysis for HPV-16/18/31 "super" probe.

According to one embodiment of the present invention there is provided a method of screening a patient for a cancer. The method generally comprises performing an amplification technique on a sample from a biopsy taken from a patient. The sample comprises cellular material, preferably nucleic acid, and the amplification technique is directed to specific amplification of a portion of a marker for a cancer. In a preferred embodiment, the marker is a human papillomavirus (HPV) sequence. In a more preferred embodiment, the cancer is breast cancer in any stage of development. The method may further include probing for the presence of an HPV sequence in the amplified sequence using an HPV specific probe.

The methods of the invention may comprise amplification of at least one HPV sequence selected from the group consisting of HPV18, HPV31, HPV33, HPV35, HPV45, HPV58, or any combination comprising at least HPV sequences. Suitable combinations include: HPV16 and at least any one of the group consisting of HPV18, HPV31, HPV33, HPV35, HPV45, HPV58; HPV18 and at least any one of the group consisting of HPV16, HPV31, HPV 33, HPV35, HPV45, HPV58; and at least any two of the group consisting of HPV18, HPV31, HPV33, HPV35, HPV45, HPV58.

With respect to probing for a specific HPV sequence, the methods of the invention may comprise probing for at least one HPV sequence selected from the group consisting of HPV18, HPV31, HPV33, HPV35, HPV45, HPV58, or any combination comprising at least HPV sequences. Suitable combinations include: HPV16 and at least any one of the group consisting of HPV18, HPV31, HPV 33, HPV35, HPV45, HPV58; HPV18 and at least any one of the group consisting of HPV16, HPV31, HPV 33, HPV35, HPV45, HPV58; and at least any two of the group consisting of HPV18, HPV31, HPV33, HPV35, HPV45, HPV58.

The samples used in the present invention may be obtained from a biopsy from a cervical intraepithelial neoplasia III (CIN III) positive patient or a CIN III negative patient. Preferably the sample is obtained from a biopsy from a patient who is not afflicted with CIN III (a non-CIN III patient). Thus the sample may first be tested/assayed for the presence of any CIN III-marker known in the art.

The sample may be derived from the patient by any method known in the art, such as, for example, any well known method for obtaining a biopsy, including the recently reported technique of breast duct lavage (Dooley W. C. et al., Lancet, 2001, 357(9265):1335-6; Evron, E. et al., Obstetrics & Gynecology, 2001, 97(4):S2, both of which are incorporated herein by reference). Numerous methods for obtaining a sample via biopsy are known in the art and include for example bite, brush, cone, cytological, aspiration, endoscopic, excisional, exploratory, incisional, percutaneous, punch, and surface biopsy. Breast duct lavage, also referred to as ductal lavage and intraductal lavage, is a relatively noninvasive procedure and enables the retrieval of breast epithelial cells that line the ductal/lobular systems of all milk ducts. Whereas a needle is used in aspiration biopsy, the technique of ductal lavage comprises use of a microcatheter which is inserted into the milk ducts through the nipple surface orifices. Saline is then flushed through the ducts to wash out epithelial cells for collection and further evaluation.

Preparation of samples for amplification is well known in the art, and any such technique may be used herein. Amplification methods are well known in the art and include techniques such as, for example, polymerase chain reaction (PCR) amplification and reverse transcription PCR (RT-PCR), as well as others. The amplified products may be detected and analyzed using any of the numerous techniques well known in the art.

The amplification technique used herein may be specific for amplification of a portion of at least one HPV sequence selected from the group consisting of HPV18, HPV31, HPV 33, HPV35, HPV45, HPV58. The amplification technique used herein may be specific for amplification of a portion of at least two HPV sequences selected from the group consisting of HPV18, HPV31, HPV33, HPV35, HPV45, HPV58. The amplification technique used herein may be specific for amplification of a portion of HPV16 and at least one HPV sequence selected from the group consisting of HPV18, HPV31, HPV33, HPV35, HPV45, HPV58.

Another embodiment of the present invention provides for a method of screening a patient for a cancer. The method generally comprises contacting cellular material together with an HPV specific probe. The cellular material is generally extracted from a sample, such as a biopsy, taken from a patient. The cellular material may be any purified or non-purified cellular material such as, for example, deoxyribonucleic acid (DNA), ribonucleic acid (RNA), polypeptides, or a combination thereof. The cellular material may be purified, either partially or wholly, using any of the purification methods well known in the art.

The HPV probes useful in the screening methods of the present invention may be any type of probe useful in detecting the presence of HPV. These probe types include, but are not limited to, a single-stranded or double-stranded oligonucleotide sequence complementary to the plus or minus strand of an HPV DNA sequence, a single-stranded or double-stranded oligonucleotide sequence complementary to a portion of an HPV mRNA sequence, and an antibody specific to an epitope of an HPV protein. Suitable examples of HPV proteins include, but are not limited to, the HPV16 E6 or HPV16 E7. Oligonucleotide sequences specific to HPV sequences are known in the art, such as, for example, those disclosed in Breast Cancer Rch. Trtmt, 53;121–135, Anticancer Rch. 19;5057–5062, J.Gen.Virol. 76:1057–1062, J.Pathol 165: 301–309, and J.Clin.Microbiol. 34: 2095–2100, with all of these articles herein incorporated by reference. Oligonucleotides may also be designed according to the Los Alamos National Laboratory Database nomenclature for the different HPV genomes, incorporated herein by reference.

Methods of detecting targeted sequences with a probe are well known in the art and are included herein. Any type of hybridization method is suitable for use in the present invention.

The screening methods of the present invention may be performed on a sample from any organism/patient capable of developing cancer. Preferably, the method of the present invention is performed on a samples taken from a mammal, more preferably a human. The patients on which the methods of the invention are used may be CIN III positive or CIN III negative. In a preferred embodiment, the patients are not afflicted with CIN III (CIN III negative). The screening methods described herein are useful in detecting numerous types of cancer, such as, for example, breast, dermal, oral, penile, vulvar cancer, and any combination thereof. In addition, the screening methods of the present invention are useful in detecting a cancer in any stage of development.

Even another embodiment of the present invention provides for a method of treating a patient afflicted with a cancer. The method generally comprises administering a composition comprising an effective amount of an antisense HPV sequence to a patient. The size of the sequence is not limited and can range in size from that of an oligonucleotide to that of a transcript. The antisense HPV sequence may comprise DNA, RNA, ribosomal RNA, or any combination thereof. The HPV may be any member of the HPV family, non-limiting examples of which include, HPV16, HPV18, HPV31, HPV33, HPV35, HPV45, HPV58, and any combination thereof. Preferred HPV's include HPV 16 and HPV 18. Non-limiting examples of combinations include: HPV 16 with at least one of HPV18, HPV31, HPV33, HPV35, HPV45, and HPV58; HPV 18 with at least one of HPV16, HPV31, HPV33, HPV35, HPV45, and HPV58; both HPV16 and HPV18 with at least one of HPV31, HPV33, HPV35, HPV45, and HPV58, and at least any two of HPV16, HPV18, HPV31, HPV33, HPV35, HPV45, and HPV58.

The HPV sequence may be expressed from a recombinant expression vector. Suitable vectors are known in the art and include, for example, mammalian expression vectors and viral vectors. Examples of viral vectors suitable for use in the present invention include: retroviruses; adenoviruses; adenoviral/retroviral chimeras; adeno-associated viruses; herpes simplex virus I or II; parvovirus; and reticuloendotheliosis virus. Other possible viral vectors may be derived from poliovirus, papillomavirus, vaccinia virus, lentivirus, as well as chimeric vectors incorporating favorable aspects of any two or more of the above viruses. Preferably, the antisense HPV sequence is expressed from a recombinant viral expression vector, such as an adeno-associated vector.

Still another embodiment of the present invention provides for a method of treating a patient afflicted with a cancer. The treatment method generally comprises administering an effective amount of a composition to a patient, wherein the composition comprises an agent that inhibits expression of at least one HPV gene. The patients of the present invention may be CIN III positive or CIN III negative. Preferably, the patient is negative for CIN III.

Mechanisms for inhibiting the expression of a gene are numerous and well known in the art and include, but are not limited to, inhibiting gene transcription, inhibiting the messenger RNA (mRNA) of a gene, inhibiting translation of an mRNA, inhibiting post-translational modification of a gene product, and inhibiting a gene product. These inhibition methods may be direct or indirect. Any of these mechanisms may be used in the present invention.

Agents that inhibit expression of at least one HPV gene suitable for use in the present invention include, an oligonucleotide or longer stretch of nucleic acid comprising antisense HPV DNA, RNA or ribosomal RNA, and an oligonucleotide or longer stretch of DNA, RNA, or ribosomal RNA comprising a sequence complementary to the plus or the minus strand of HPV DNA. The HPV targeted in the present invention may be any HPV family member, non-limiting examples of which include, HPV16, HPV18, HPV31, HPV33, HPV35, HPV45, HPV58, and any combination thereof. Preferred HPV's include HPV 16 and HPV 18. Non-limiting examples of combinations include: HPV 16 with at least one of HPV18, HPV31, HPV33, HPV35, HPV45, and HPV58; HPV 18 with at least one of HPV16, HPV31, HPV33, HPV35, HPV45, and HPV58; both HPV16 and HPV18 with at least one of HPV31, HPV33, HPV35, HPV45, and HPV58, and at least any two of HPV16, HPV18, HPV31, HPV33, HPV35, HPV45, and HPV58.

Administration of the compositions of the present invention to a recipient may be by any method known in the art. Thus, administration of the present invention to a recipient may be by a route selected from oral, parenteral (including, subcutaneous, intradermal, intramuscular, and intravenous) and rectal. For increased efficacy, the compositions of the present invention may be administered via localized delivery to the targeted tissue, such as, for example, breast tissue in the case of breast cancer. A modified breast duct lavage technique, also known as ductal lavage, may be used for localized directly of the anticancer compounds and compositions of the present invention to a breast duct and breast epithelial cells. Similar to the technique for ductal lavage, a microcatheter may be inserted into a nipple surface orifice and subsequently into a milk duct. However, instead of simply flushing the duct in order to obtain epithelial cells, as is done with ductal lavage, the microcatheter may be used for localized delivery of a composition of the invention directly to the breast duct and breast epithelial cells.

Yet another embodiment of the present invention provides for a method of treating a patient afflicted with a cancer. The cancer may be any cancer in any stage of development. In a preferred embodiment, the cancer is breast cancer. In addition, the patient may be CIN III positive or CIN III negative. Preferably, the patient is negative for CIN III. The treatment method generally comprises administering an effective amount of a composition to a patient, wherein the composition comprises an agent that specifically inhibits an HPV protein. Examples of HPV proteins to target for inhibition include the HPV16 E6 protein and the HPV16 E7 protein. Inhibition of a protein can be by any of the methods known in the art, such as, inhibition of gene expression, targeting a protein with an antibody, inhibition of post-translation modification, and inhibition of protein stability and half-life. A preferred agent for use in the treatment method of the present invention is an antibody specific for interaction with an epitope of an HPV protein, such as HPV16 E6 protein or HPV16 E7 protein.

Additional inhibitory agents suitable for use in the compositions and methods of the invention include agents wherein the agent is a DNA, cDNA, RNA, ribosomal RNA, or polypeptide sequence. Suitable examples of such agents include, an antisense HPV sequence which inhibits transcription or translation of a HPV gene or gene product, transcription factors which decrease expression of an HPV gene, factors which affect translation of an HPV mRNA, factors which decrease the stability/half-life of an HPV mRNA molecule, factors which decrease the stability/half-life of an HPV polypeptide, and factors which interact with an HPV polypeptide, such as a polypeptide encoding an antibody which specifically interacts with an epitope of a HPV. The material and methods for producing these types of inhibitors (DNA, cDNA, RNA and polypeptide) are known in the art and are included in the present invention.

For example, expression vectors expressing a sequence inhibitory to transcription of a HPV gene or expressing a sequence inhibitory to translation of a HPV mRNA are within the scope of the HPV inhibitors defined herein. Expression vectors suitable for the present invention may comprise an antisense HPV sequence, or a sequence encoding a negative regulator of transcription of a HPV gene.

Even still another embodiment of the present invention provides for a method of treating a patient afflicted with a cancer. The method generally comprises transfecting dendritic cells (DCs), primed T cells or a combination thereof, into a patient, wherein the dendritic cells have been altered to stably produce an HPV antigen. The basis for using DC cells for human immunotherapy has recently been established as described in Young, J. W., and Inaba, K. (1996) DCs as adjuvants for class I manor histocompatibility complex-restricted antitumor immunity. J. Exp. Med. 183:7–11, and Santin, A. D., Hermonat, P. L., Ravaggi, Al, Chiriva-Internati, M., Hiserotdt, J. C., Pecorelli, S., and Parham, G. P. (1999) Kinetics of expression of surface antigens during the differentiation of human dendritic cells versus macrophages. Immunobiology 200, both of which are incorporated herein by reference.

Briefly, DCs are presently believed to be the most effective antigen presenting cells for activating naive T cells. Blood monocytes can be induced to differentiate in to DCs by treatment with at least one cytokine. DCs when pulsed with antigen (Ag) results in a class I restricted cytotoxic response against the Ag. In most DC-pulsing protocols of the art, antigen proteins to be targeted are transfected into DCs for immune stimulation. These DC protocols may be used herein. However, both the antigen to be presented by the Dcs, and the cytokines used to generate the DCs degrade with time as a reflection of their half-lives. Thus, a more effective technique for pulsing/treating the DCs may be the in situ generation/production of the antigen protein such as at least a portion of an HPV protein, and/or a cytokine within and by the DC itself. By delivering a tumor-antigen gene and/or cytokine gene directly in the DC, a stable and continuous production of the proteins may be achieved.

Thus, a recombinant viral vector that has been genetically manipulated to comprise a portion of a HPV gene and thus expresses at least a portion of an HPV gene may be used to infect monocyte precursors which have been acquired from a blood sample of a patient. The infected monocytes are then induced to differentiate into DCs by treatment with at least one cytokine. Examples of suitable cytokines include, but are not limited to IL-2, IL-4, other interluekins, GM-CSF, TNF, INF, and any combination thereof. The dendritic cells may also stably produce a cytokine from a recombinant vector.

Techniques for transferring genes are well known in the art, and any of those techniques may be used to produce dendritic cells that stably produce the antigen of choice. Preferably, a recombinant retrovirus such as, for example, an adeno-associated virus (AAV) that has been genetically manipulated to comprise a portion of an HPV antigen-encoding gene is used to infect monocyte precursors which are then induced to differentiate into DCs. In a preferred embodiment, an AAV-HPV is used to infect monocytes which are then induced to differentiate into DCs.

Materials and techniques for the design, generation and production of recombinant retroviral vectors and genomes are well known in the art. All such standard DNA materials, techniques and methodologies are suitable for use herein. An example of a recombinant retroviral vector suitable for use herein may comprise the general purpose p5 transcriptional promoter to express the antigen genes. Recombinant adeno-associated virus (rAAVs) may be produced by first generating high producer cell lines to make high-titer virus stocks, as known in the art. As also known by one of skill in the art, these stocks may then be CsCl purified and titered by quantitating the amount of encapsidated genomes (virus) by Southern blot.

Suitable non-limiting examples of HPV's useful in the present invention include, HPV16, HPV18, HPV31, HPV33, HPV35, HPV45, HPV58, and any combination thereof. Preferred HPV's include HPV 16 and HPV 18. Non-limiting examples of combinations include: HPV 16 with at least one of HPV18, HPV31, HPV33, HPV35, HPV45, and HPV58; HPV 18 with at least one of HPV16, HPV31, HPV33, HPV35, HPV45, and HPV58; both HPV16 and HPV18 with at least one of HPV31, HPV33, HPV35, HPV45, and HPV58, and at least any two of HPV16, HPV18, HPV31, HPV33, HPV35, HPV45, and HPV58. For example, for HPV16 the DCs stably produce HPV 16 E6, HPV 16 E7 or both. Any portion of the HPV, full-length or not, may be utilized herein.

The treatment methods of the present invention may be performed on any organism having a cancer. Preferably, the methods of the present invention are performed on a human. The patient may be positive for CIN III or negative for CIN III. In a preferred embodiment, the screening methods are carried out on patients who have tested negative for CIN III, and/or are not afflicted with cervical intraepithelial neoplasia (CIN III). The treatment methods described herein may be useful in treating numerous types of cancer, such as, for example, breast, dermal, oral, penile, vulvar cancer, and any combination thereof. In addition, the treatment methods of the present invention may be against a cancer in any stage of development.

The compositions and methods of the present invention are suitable for any individual afflicted with a cancer. Suitable individuals include mammals such as, humans, dogs, cats, horses, cows, sheep, goats, pigs, rats and mice. As mentioned, preferably the patient is human. The compositions and methods of the present invention are also suitable for use in any tissue or cell line that serves as a model for the study of cancer. Thus the present invention is useful to medical and health care professionals including, medical doctors, and veterinarians, as well as research scientists.

It should be noted that the present invention encompasses any and all methods for screening a patient for a cancer, wherein the method comprises detection of an HPV. Any and all methods for treating a patient having a cancer, wherein the method comprises inhibition of an HPV are also within the scope of the invention.

The compositions useful in the methods of the present invention further comprise a pharmaceutically acceptable carrier/vehicle. Pharmaceutically acceptable carriers/vehicles are known in the art and include aqueous solutions, non-toxic excipients, including salts, preservatives, buffers and the like, propylene glycol, polyethylene glycol, vegetable oil, injectable organic esters such as ethyloleate, water, saline solutions, parenteral vehicles such as sodium chloride and Ringer's dextrose, glycerol, lipids, alcohols.

Compositions of the present invention may be in any form known in the art, such as an orally digestible form, a sterile injectable form, forms suitable for delayed release, and forms that are enterically coated. Compositions of the invention may be in solid forms, including, for example, powders, tablets, pills, granules, capsules, sachets and suppositories, or may be in liquid forms including solutions, suspensions, gels and emulsions.

The compositions and methods of the present invention may be administered to a recipient/patient as a single dose unit, or may be administered in several dose units, for a period ranging from one day to several years. The dose schedule is dependent upon at least the severity of the glomerular disorder, as well as the mode of administration.

The effective dose of the compositions of the present invention is further dependent upon the body weight (BW) of the recipient/patient and also upon the chosen inhibitor. Generally the compositions of the present invention are administered orally or intravenously.

Even still another embodiment of the present invention provides for a kit for screening a patient for a cancer. Generally the kit comprises a probe that is specific for the detection of an HPV family member. The HPV-specific probe may be a single-stranded oligonucleotide sequence, a double-stranded oligonucleotide sequence, a polypeptide, or any combination thereof. The HPV may be any HPV family member, non-limiting examples of which include, HPV16, HPV18, HPV31, HPV33, HPV35, HPV45, HPV58, and any combination thereof. Preferred HPV's include HPV 16 and HPV 18. Non-limiting examples of combinations include: HPV 16 with at least one of HPV18, HPV31, HPV33, HPV35, HPV45, and HPV58; HPV18 with at least one of HPV16, HPV31, HPV33, HPV35, HPV45, and HPV58; both HPV16 and HPV18 with at least one of HPV31, HPV33, HPV35, HPV45, and HPV58, and at least any two of HPV16, HPV18, HPV31, HPV33, HPV35, HPV45, and HPV58.

The kit of the present invention is useful in screening any organism capable of developing a cancer. Preferably the sample to be screened is derived from a human patient. The patient may be CIN III positive or CIN III negative, preferably the patient is CIN III negative. The kit of the present invention may be useful in detecting a cancer that is in any stage of development, and may be useful in detecting any cancer, such as, for example breast, dermal, oral, penile, vulvar cancer, and any combination thereof.

Even yet another embodiment of the present invention provides a composition for treating a patient having a cancer. Generally, the composition comprises an effective amount of an HPV sequence. The size of the sequence is not limited. The HPV sequence of the composition may comprise single-stranded nucleic acids, double-stranded nucleic acids, polypeptides, and any combination thereof. The HPV sequence may be any one or any combination of HPV family members. Suitable HPV family members include but are not limited to, HPV 16, HPV 18, HPV 31, HPV 33, HPV 35, HPV 45, HPV58, and any combinations thereof. Suitable combinations include: HPV16 and any one of the group consisting of HPV 18, HPV 31, HPV 33, HPV 35, HPV 45, and HPV58; HPV 18 and any one of the group consisting of HPV 16, HPV 31, HPV 33, HPV 35, HPV 45, and HPV 58; HPV 16 and HPV 18; HPV 16 and HPV 18 and any one of the group consisting of HPV 31, HPV 33, HPV 35, HPV 45, HPV 58, and any combinations thereof.; HPV 16, HPV 18 and HPV 33, and any one of the group consisting of HPV 31, HPV 35, HPV 45, HPV 58, and any combinations thereof, and at least any two of the group consisting of HPV 16, HVP 18, HPV 31, HPV 33, HPV 45 and HPV 58.

All references cited herein, including research articles, all U.S. and foreign patents and patent applications, are specifically and entirely incorporated by reference.

EXAMPLES

The following examples are provided to illustrate the present invention. These examples are not intended to and do not limit the scope of the claims of the present invention, and should not be so interpreted.

Example 1

Analysis of Breast Cancer Tissue for Presence of HPV via PCR.

In the present example, total DNA was isolated from breast cancer tissues and analyzed for the presence of HPV by use of PCR amplification. The amplification targeted the L1 gene and was broad spectrum, thus allowing for amplification of many different HPV types.

Patients, Breast Cancer Specimens, and DNA Isolation 17 women with breast cancer receiving examinations and treatment at the University of Arkansas for Medical Sciences (UAMS) from May 1999 to October 1999. Portions of needle biopsy tissue was fixed in a Phosphate Buffered Saline: Ethanol (1:1) solution soon after they were acquired. All of the specimens were stored at −80° C. The specimens were processed by grinding, and total cellular DNA was isolated from the specimens by pelleting and resuspending them in lysis buffer (0.5 mg/ml Proteinase K, 0.5% SDS, 0.5 mM EDTA, 0.5 mM Tris-HCL, pH 7.4). After incubation overnight at 37° C., the total cellular DNA was extracted by phenol/chloroform twice, and then precipitated by ethanol. The DNA was stored at −80° C. before use. The research has been approved by the UAMS Human Research Advisory Committee and undertaken in a P2 laboratory.

Polymerase Chain Reaction (PCR) Primer Sets

An HPV L1-targeting consensus primer set has been described elsewhere and was designed to amplify a 450-base segment of HPV L1 gene sequence (Bauer, H. M., et al., JAMA 1991; 265: 472–7). These primers enable PCR amplification of most genital HPV types. A second PCR primer set targeting E6–E7 region has also been described by elsewhere (Fujinaga, Y, et al., J. Gen. Virol. 1991; 72: 1039–1044). These primers allowed for the amplification of most of the cancer associated HPVs. PCR amplification was carried out as described by Hermonat et al. (Hermonat P; et al., Virus Genes 1997; 14:13–17). Positive controls included various amounts of the indicated cloned HPV genome, while negative controls included all reagents except specimen DNA.

In order to identify potential contamination from recombinant plasmids carrying HPV sequences, which are used in the inventors' laboratories, PCR amplification was carried out with pBR322 plasmid targeting primers. The primers were designed to amplify a 414-base segment of pBR322 sequence (upstream primer 5'-ATACCTGTCCGCCTTTCTC-3', and downstream primer 5'-AATCTGCTGCTTGCAA AC-3'), containing the origin of replication (ori). The controls included known quantities of pBR322, as low as ten molecules.

PCR-Dot Blot Hybridization

Amplification of DNA samples was carried out in 100 µl reactions using approximately 5 µg of the total cellular DNA, 0.2 mM of each dNTP, 1 µM of each primers, and 2.5 U of Taq iPolymerase according to the suppliers instructions (Fisher Scientific Co., Pittsburgh, Pa.) instructions. After 5 minutes at 94° C., each sample was subjected to the following amplification cycle: 55 seconds at 94° C., 1 minutes at 60° C., and 50 seconds at 72° C. for 35 cycles, then 10 minutes at 72° C. in the final cycle.

The dot blotting was carried out with all of the PCR products as described by Hermonat et al. (Hermonat P; et al., Virus Genes 1997; 14:13–17). Briefly, 5 µl of PCR products was first denatured by the addition of 10 µl of 0.4 N NaOH, incubated for 10 minutes, and then ice-bath was done for 5 minutes. After the samples were reneutralized by the mixing of 200 µl Tris-HCL, pH 7.0, 1.5 M NaCL, the samples were added immediately to a dot blot apparatus under suction. Multiple nylon membranes were generated to be analyze by one of several $^{32}$P-labeled probes. The HPV probes were made with Primer-a-Gene Labeling System (Promega Co.), a random prime labeling kit according to the supplier=s instructions, which templates were HPV 16, 18 and 31 genomic DNA respectively.

The membranes were analyzed with the radiolabeled full length HPV or pBR322 DNA sequences as indicated. The membranes were soaked in hybridization solution (100 μg of denatured salmon sperm DNA, 1% SDS, 1M NaCL, 10% dextran sulfate) and incubated at 65° C. overnight. After hybridization, the membranes were first washed by 2×SSC twice at room temperature for 10 minutes, and then washed by 2×SSC and 1% SDS twice at 55° C. (super probe) or 65° C. (all others) for 30 minutes.

FIG. 1 provides the results of an assay in which PCR products were dot blotted and probed with an HPV—16/18/31 "super"-probe. As seen in FIG. 1, of the breast cancer specimens, six (B2, B4, B10, B13, B15, B17) were positive for HPV.

Figure 2:
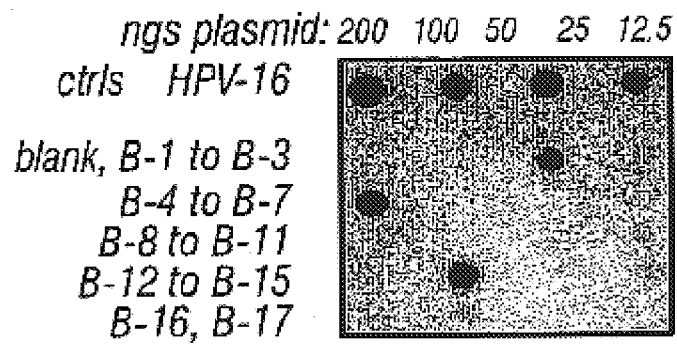
FIG. 2 provides results from a PCR/Dot blot analysis for HPVs using an L1 targeting primer set and probing with HPV-16 sequences.
Figure 3:
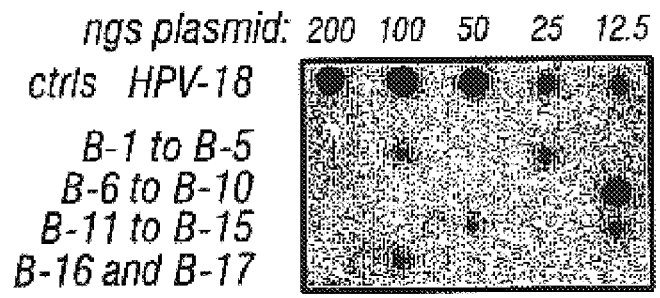
FIG. 3 is a Polymerase Chain Reaction (PCR)/Dot Blot Hybridization analysis for HPVs in breast cancer specimens using an L1 targeting primer set and probing with HPV-18 probe.
Figure 4:
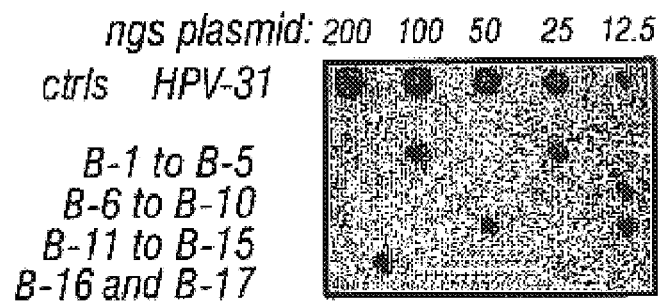
FIG. 4 is a Polymerase Chain Reaction (PCR)/Dot Blot Hybridization analysis for HPVs in breast cancer specimens using an L1 targeting primer set and probing with HPV-31 probe.

Next, the PCR products were probed with a probe specific for HPV-16 only (FIG. 2), a probe specific for HPV-18 only (FIG. 3), and a probe specific for HPV-31 (FIG. 4) only. As can be seen in FIG. 2, the results for the HPV-16-specific probe revealed that specimens B2, B4, and B13 gave a strong signal, suggesting that B2, B4, and B13 are most likely HPV-16. The results from the HPV-18 probe (FIG. 3) revealed that all six specimens were positive for HPV-18 (B2, B4, B10, B13, B15, B17), but that B15, in particular, gave a very strong signal suggesting that this specimen was most likely HPV-18. The results for HPV-31 probing (FIG. 4) revealed that all of the six known HPV-positive specimens were weakly positive. This verifies that the six specimens are HPV positive, but also further suggests that the specimens are most likely not HPV-31.

Figure 5:
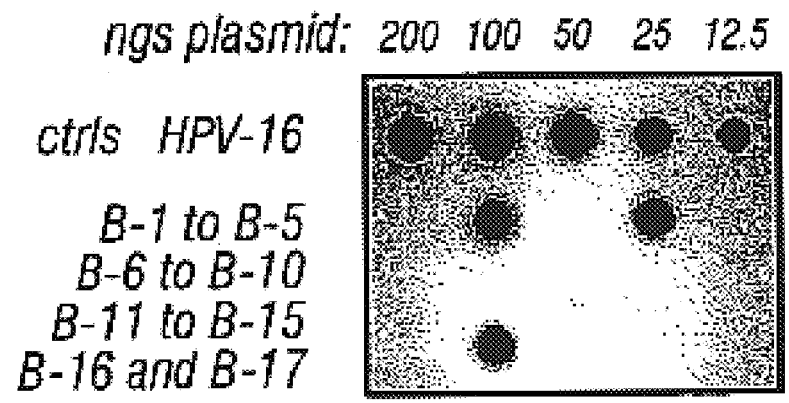
FIG. 5 provides results from a PCR/Dot blot analysis for HPVs using an E6-E7 junction targeting primer set and probing with HPV-16 sequences.

The results from a PCR/Dot blot analysis for HPV-16 using an E6-E7 junction targeting primer set and probing with HPV-16 sequences are shown in FIG. 5. The dot blotted PCR products were probed for HPV-16 and the membrane washed at 65° C. Positive controls are at the top. An unlabeled negative control is one row below on the far left. Note that this primer/probe combination appears to pick up the same specimens as identified by the L12 primer set and HPV-16 probe (compare to FIG. 2) (B2, B4, B13).

Figure 6:
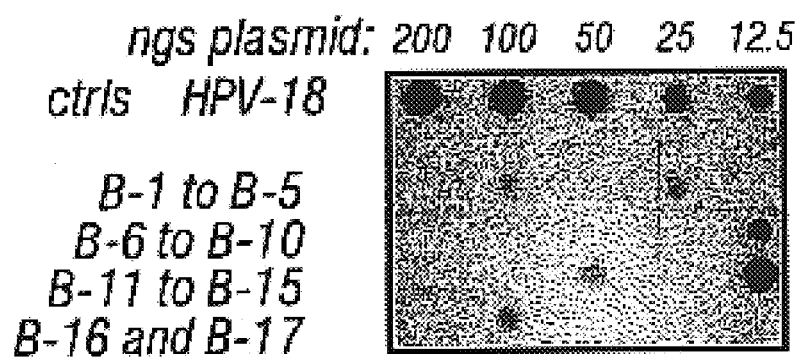
FIG. 6 provides results from a PCR/Dot blot analysis for HPVs using an E6-E7 junction targeting primer set and probing with HPV-18 sequences.

The results from a PCR/Dot blot analysis for HPV-18 using an E6-E7 junction targeting primer set and probing with HPV-18 sequences are shown in FIG. 6. Positive controls are at the top. An unlabeled negative control is one row below on the far left. Note that this probe identifies all of the specimens identified by the super probe and the L1 products, however B10, and B15 are identified most strongly.

Figure 7:
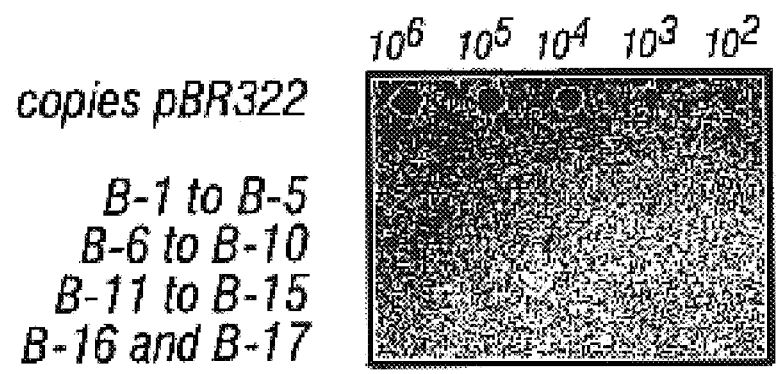
FIG. 7 is a PCR/Dot Blot Hybridization analysis for contaminating plasmids by using a primer set which targets the pBR322/ColE1 ori region.

Experiments were then carried out in order to eliminate the possibility of false positive signal from the tissue sample due to any type of plasmid contamination. As shown in FIG. 7, these samples were further analyzed for plasmid sequences using PCR primers which targeted the ColE1 plasmid origin of replication (ori) region. Essentially all plasmids in use today and in our laboratory are based upon this ori. A dot blot hybridization analysis, probed with $^{32}$P-pBR322 is shown in FIG. 7. As can be seen no contamination from plasmid DNA was observed in any of the samples.

In cervical cancer the HPV DNA is often chromosomally integrated. To determine the state of the HPV DNA in breast cancer, 10 μgs of genomic DNA was digested with Bam HI or Xho I. HPV-16 and HPV contain a single Bam HI site, and no Xho I sites. The restricted DNA, along with undigested DNA, were agarose gel electrophoresed, Southern blotted and probed with $^{32}$P-HPV-16 DNA. The Southern Blot revealed hybridization of the probe with an 8 kb band, consistent with episomal DNA. Only in the cervical swab specimen C2 was there significant evidence of chromosomal integration of the HPV DNA.

Example 2

Figure 8A:
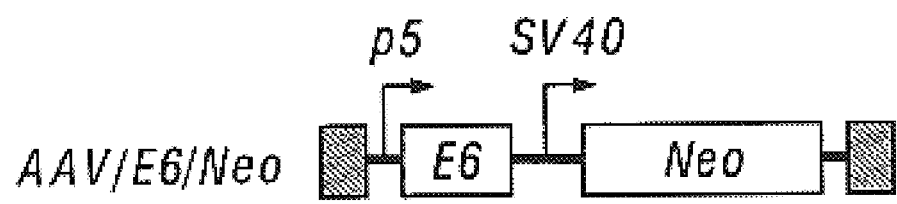
FIG. 8A shows a structural map of the AAV/NE6/NEO (a.k.a. d16-95/E6$^{p5}$/NEO$^{sv40}$) virus with the names of the components at the top.

Construction of the AAV/E6/Neo Genome, Generation of Virus Stocks, and Titering of Virus Stocks The AAV/E6/Neo genome was constructed as a plasmid, in a similar manner to the construction of the AAV/GM-CSF/Neo viral genome as described by Liu (Liu. Y., et al., J. Inf. Cytok. Res. 2000; 20:21–30), incoporated herein by reference. However, instead of the GM-CSF gene, the HPV-16 E6 open reading frame was cloned by PCR amplification using Pfu polymerase and ligated into the vector. A structural map of the AAV/E6/Neo vector used in this study is shown in FIG. 8A. In this construct the E6 gene is expressed from the AAV p5 promoter, which is known to be active in DC. An AAV/E7/Neo vector was also made in this study (not shown). In the E7 construct, the E7 gene is expressed from the AAV p5 promoter.

High titer rough (non-purified) rAAV virus stocks were generated in a two-step process, using the complementor plasmid ins96-0.8, and titered as described previously by Hermonat et al., and Li et al. (Hermonat, P., et al., FEBS Let. 1997: 407:78–84; and Liu. Y., et al., J. Inf. Cytok. Res. 2000; 20:21–30), incoporated herein by reference.) In order to generate purified rAAV virus, the technique described by Auricchio et al. was used (Human Gene Therapy 2001; 12:71–76). Briefly, the virus solution treated by DNase I (Promega Co.) was incubated with 0.5% deoxycholic acid (Sigma Co.) for 30 minutes at 37° C. After filteration the solution was applied on a heparin-agarose column (Sigma Co.). The matrix was washed twice with 25 ml of 0.254M NaCl-PBS, pH 7.4, and then eluated with 15 ml of 0.554M NaCl-PBS, pH 7.4. The eluate was then concentrated to about 1 ml using a Millipore Biomax-100K NMWL filter device and cetrifugation.$^{50}$. Purity of the viral preparation (100 ul) was assessed on 4–20% SDS-polyacrylamide gel run. The proteins were detected by Coomassie staining. The titer of purified virus was calculated by dot blot and determined to be $1 \times 10^{11}$ encapsidated genomes per ml.

Figure 8B:
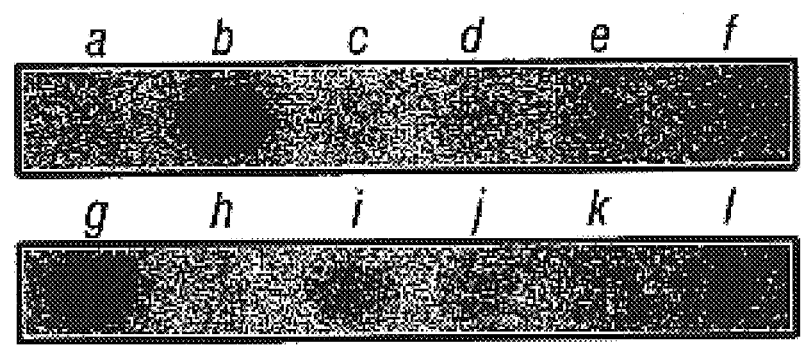
FIG. 8B shows the analysis of various 293/vector producer cell lines.
Figure 8C:
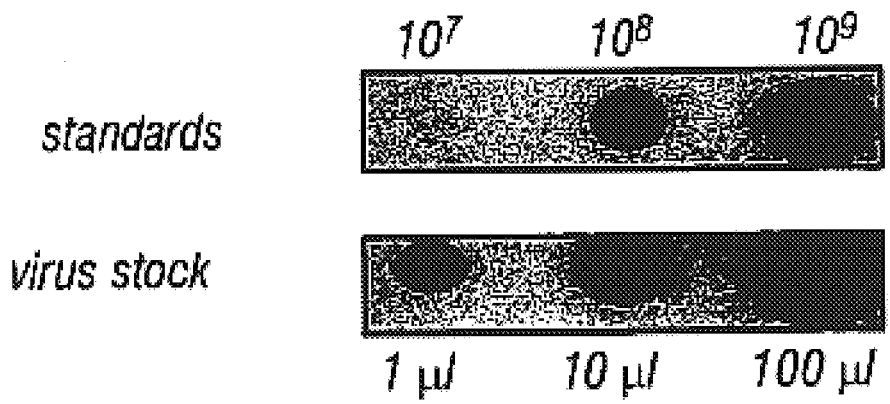
FIG. 8C shows a titering analysis of the AAV/E6/Neo virus stock used in this study.

AAV/E6/Neo virus stock was generated by the two step process mentioned above, and a comparison of various G418 resistant producer cell lines, by dot blot hybridization, is shown in FIG. 8B. The titering of the non-purified virus stock, in encapsidated genomes (eg) per ml of this virus stock, by dot blot hybridization is shown in FIG. 8C (about $10^{11}$ eg/ml).

Cells Used in this Study

The primary cervical cancer cell lines, CA1 (patient 1) and CA2 (patient 2), have been described previously, both containing HPV-16 DNA, and were approximately 10 passages from initial isolation (Santin, A. D., et al., J. Virol., 1999: 73: 5402–5410). These cells were grown in Keratinocyte-SFM supplemented with epidermal growth factor and bovine pituitary extract (Gibco BRL/Life Technologies). Human Leucocyte Antigen (HLA) typing of these cells gave haplotypes of HLA A1 for both CA1 and CA2, respectively. Mo and DC were derived from peripheral blood mononuclear cells (PBMC). PBMC were separated by routine Ficoll gradient method from fresh blood drawn from healthy persons. The normal donor had a haplotype of HLA A1, compatible with the target cancer cells. The PBMCs were inoculated into six-well culture plates and incubated with two milliliters of AIM-V medium for two hours at 37°

C. and 5% $CO_2$. At that time non-adherent cells were removed by carefully washing the monolayer three times with phosphate buffered saline (PBS, pH 7.0).

Infection of Mo/DC with AAV Virus and Treatment with Cytokines

Immediately after the removal of the non-adherent cells, the adherent Mo were infected (pulsed) with 0.5 ml of virus stock (~5×10$^{10}$ encapsidated genomes) when using the non-purified virus, or 10$^7$ encapsidated genomes when using the purified virus. After two hours incubation the medium/virus solution was removed, the cells were washed with AIM-V, and finally fed with AIM-V medium. The infection protocol is outlined in FIG. 8D. The Mo/DC precursors were infected with 0.5 ml of virus stock or lysate at days 0, 3, and 5. Throughout this time period the Mo/DC culture was treated with human GM-CSF (LEUKINE®, Immunex Corporation, 1.4×10$^6$ IU/250 µgs) at a final concentration of 800 IU/ml. At day three, to induce the maturation of Mo into DC, human interleukin 4 (IL-4, R & D SYSTEMS Co.) at 1000 IU/ml was added to the medium. Finally, at day 5, recombinant human interleukin 2 (IL-2, R & D SYSTEMS Co.) at 10 U/ml was added.

Generation of Bacterial E6 Protein and Lipofection of Mo/DC

GST-E6 protein was generated in a similar manner to previous generation of GST-E7.[34] The Mo/DC were lipofected (pulsed) with 15 µg of GST-E6 on day 5 as previously described (Santin, A. D., et al., J. Virol., 1999: 73: 5402–5410). The treatment of the protein pulsed Mo/DC with cytokines was the same as the virus infected DC.

mRNA Isolation and RT-PCR Analysis for E6 Expression

E6 mRNA expression was measured by RT-PCR amplification along with a cellular mRNA control. Total RNA was isolated from mock (lysate) infected and AAV/E6/Neo infected Mo/DC using Trizol reagent (GIBCO BRL Life Technologies Inc.), according to the manufacturer's protocol and treated with 5U/µg of RNase-free DNase I (Promega Co.) at 37° C. for 1 hour. Messenger RNA was then separated using the Oligotex mRNA Mini Kit (QIAGEN Inc.) according to the supplier's instruction. The first-strand cDNA synthesis was performed at 37° C. for 1 hour in a final volume of 25 µl reaction buffer [1 µg mRNA; 50 mM Tris-HCl, pH 8.3; 75 mM KCl; 3 mM $MgCl_2$; 10mM DTT; 0.5 µg oligo(dT)$_{15}$ (Promega Co.); 0.5 mM each of the four dNTPs; 30U of RNasin (Promega Co.) and 200U of M-MLV Reverse Transcriptase RNase H Minus (Promega Co.)]. PCR amplification of the cDNA was performed in 100 µl reaction volume which contained 2.5U Taq DNA polymerase (Fisher Scientific Co.); 10 mM Tris-HCl, pH 8.3; 50 mM KCl; 2 mM $MgCl_2$; 0.2 mM each of the four dNTPs; 1 µM of each upstream and downstream primer specific for the cDNA template and 10 µl cDNA template. The E6 primer set used was 5'-ACCACAGTTATGCACAGAGC-3' and 5-AGGACACAGTGGCTTTTGAC-3', which targeted amplification of the HPV-16 sequences from nt 139 to 420. A control RT-PCR analysis of expression of the housekeeping gene TFIIB was also undertaken with the primer set 5'-GTGAAGATGGCGTCTACCAG-3' and 5'-GCCTCAATTTATAGCTGTGG-3', which amplified nt 356–1314 of that mRNA. To insure that DNA wasn't contributing to the results, a direct PCR was also undertaken. The products were then analyzed on an agarose gel, stained with ethidium bromide, and visualized by ultraviolet light.

Figure 8D:
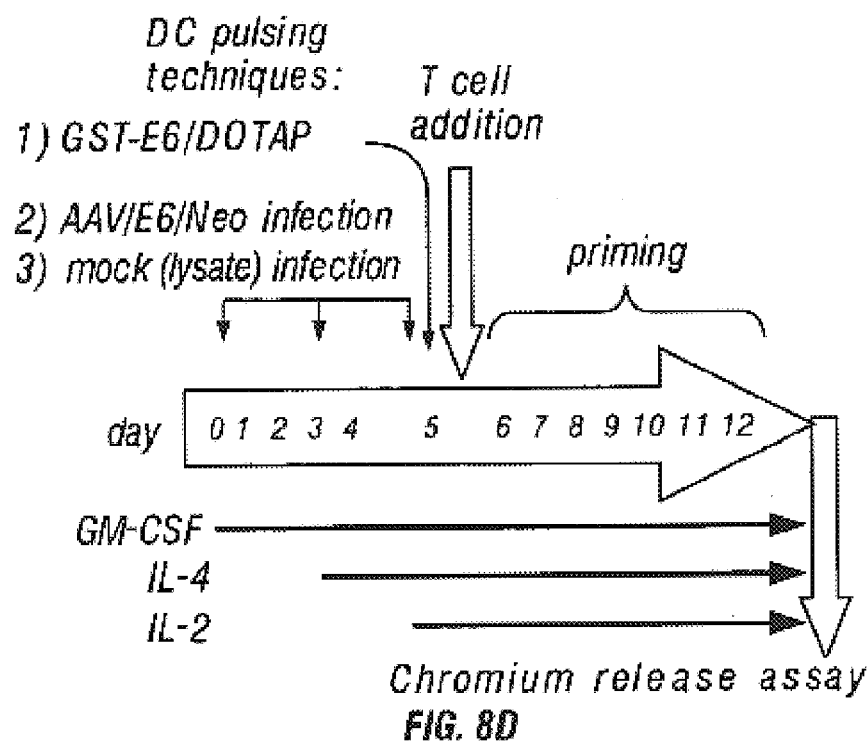
FIG. 8D shows a graphic description of the experimental protocol.
Figure 9:
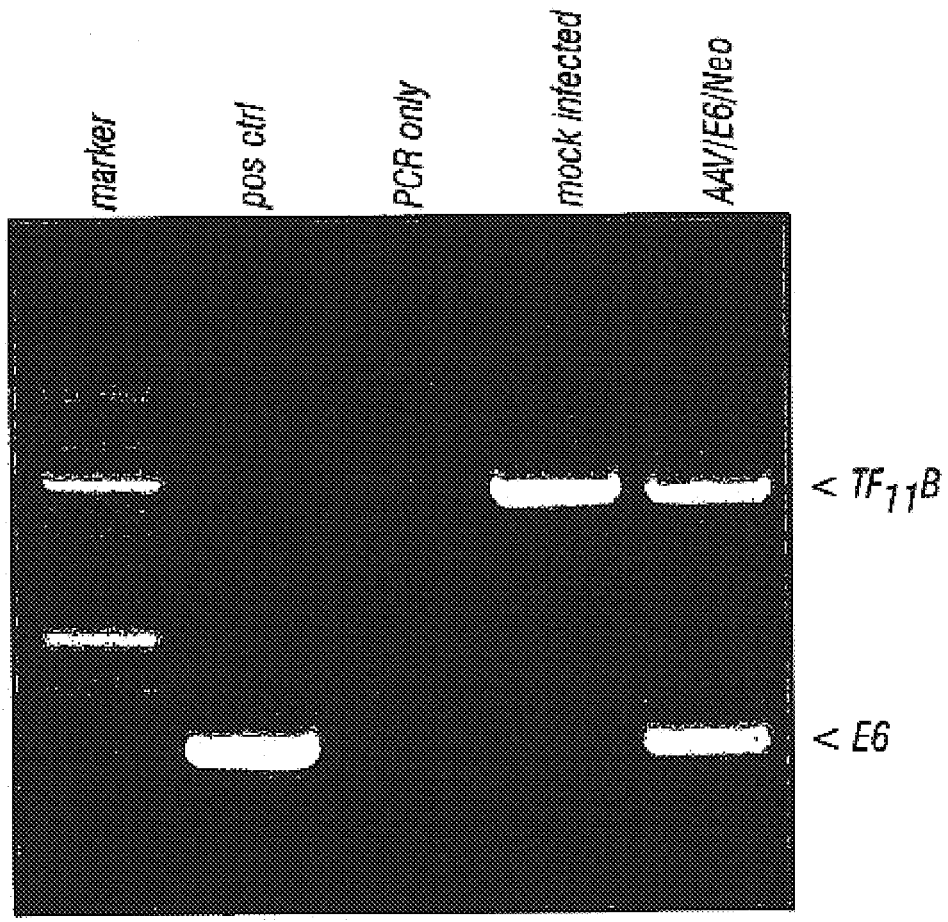
FIG. 9 provides E6 mRNA expression in infected DC.

In these studies three infections were undertaken as indicated in FIG. 8D. After AAV infection and GM-CSF treatment, at day three, the cells were finally treated with IL-4 to induce differentiation into DC. The transduction of the Mo/DC population was analyzed by observing RNA expression of the E6 transgene. Poly-adenylated RNA was isolated from AAV/E6/Neo infected and mock-infected DC cultures at day 10 (after IL-4 introduction and differentiation into DC) and was analyzed for E6 mRNA by RT-PCR. Expression of the cellular $TF_{II}B$ gene was also undertaken as a control. The results, shown in FIG. 9 demonstrate that E6 expression only takes place in the virally infected DC. In FIG. 9, the positive contro was the PCR product resulting from the Aav/E6/NEO vector plasmid as a template. Another control was PCR analysis of RNA from cells infected by AAV/E6/Neo virus. A final control included the analysis of cellular $TF_{II}B$ RNA. Note that only RNA from cells infected with AAV/E6/Neo virus resulted in an appropriate E6 RT-PCR sized product, while mock and PCR amplification of the RNA from cells infected by AAV/E6/Neo virus did not give a product, indicating lack of contaminating DNA.

Intracellular Staining for E6.

The protocol used was adapted from that described by Pala et al., (Immunology 2000; 100:209–216). The Mo/DC were infected with virus or lipofected with protein as described above. Cells were then treated with IL-4 and GM-CSF under standard conditions. Seven days after infection/lipofection the cells were harvested, washed and fixed with 2% paraformaldehyde in PBS for 20 min at room temperature. The cells were washed and permeabilized with PBS/1% BSA/0.5% saponin (S-7900, Sigma) for 10 min at room temperature. Cells were stained with anti-HPV-16/18 E6 (Chemicon Inc., Temecula, Calif.; Cat no MAB874) plus FITC-anti-mouse-Ig (Becton Dickinson Inc., cat no 554001) and analyzed by flow cytometry.

Figure 10A:
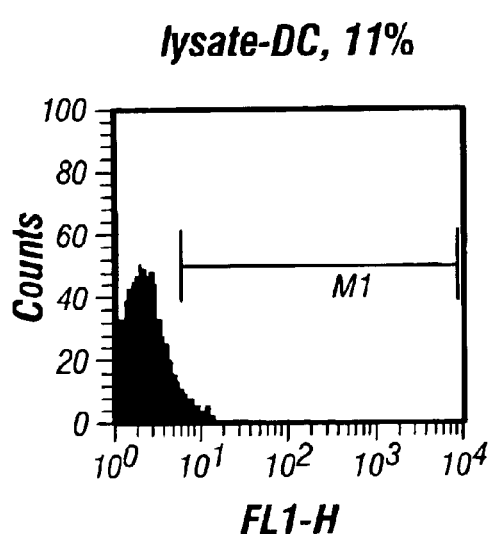
FIG. 10 provides the efficiency of Mo/DC-pulsing analyzed by intracellular staining.
Figure 10B:
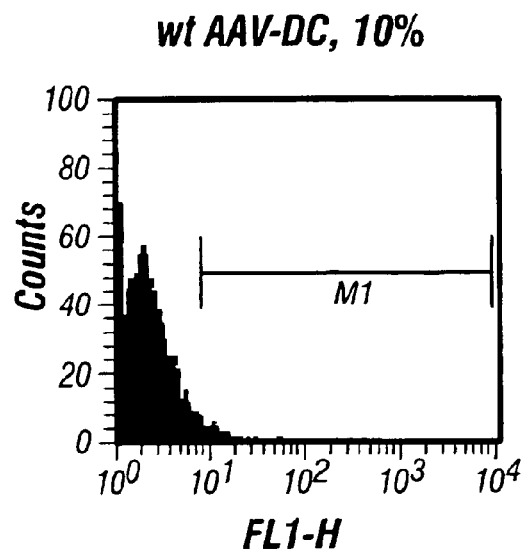
Figure 10C:
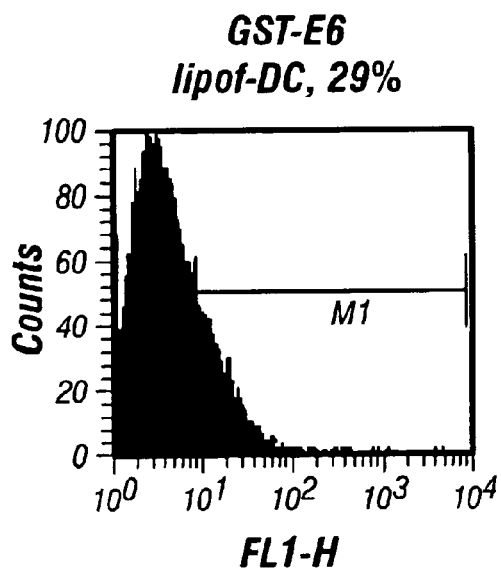
Figure 10D:
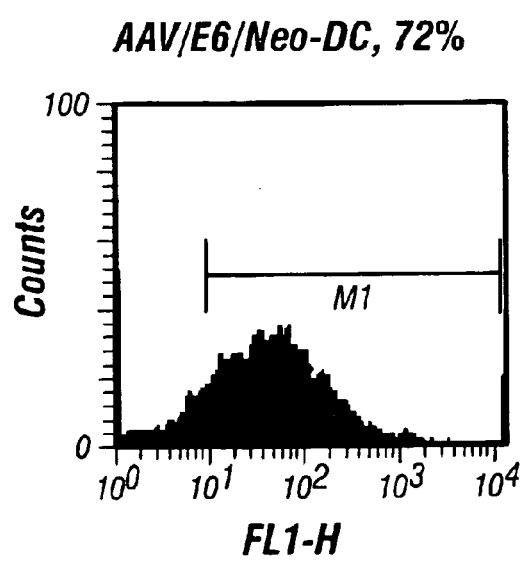

The efficiency of virus/gene and lipofection/protein-pulsing of Mo/DC was analyzed and compared by intracellular staining. The cells were analyzed four days after pulsing. The results, shown in FIG. 10, demonstrate that AAV/E6/Neo infection of Mo resulted in a much higher percentage of cells containing intracellular E6 protein than direct protein-pulsing (72% to 29%). FIG. 10A provides the results from lipofection, 10B provides the results from infection. Mo were pulsed (infection or lipofection) as indicated, treated with cytokines, and analyzed for E6 protein by intracellular staining on day 4 as described in the Materials and Methods section. Note that AAV/E6/Neo infection/pulsing gave the highest levels of E6 positive cells compared to protein lipofection (72% versus 29%)

Detection of Viral Integration by PCR/Southern Blot Analysis

Figure 11:
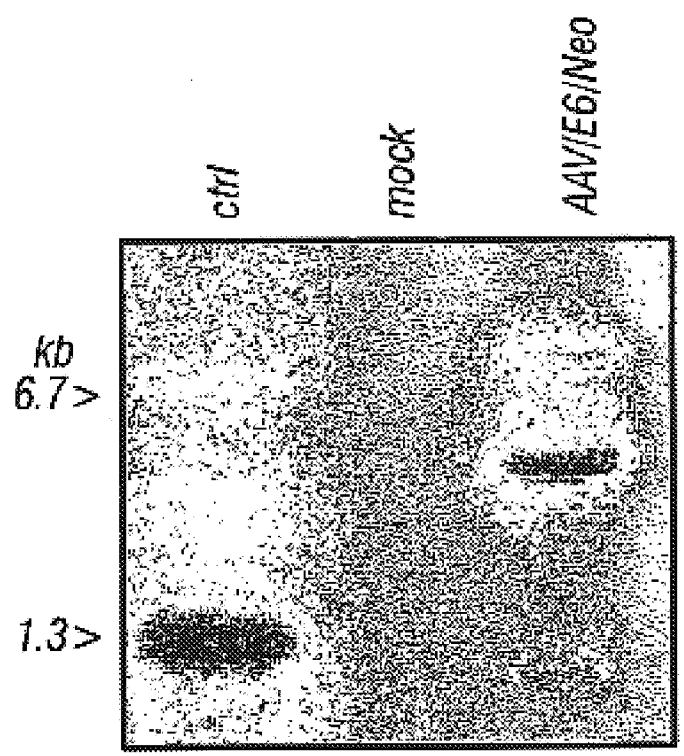
FIG. 11 shows the amount of chromosomal integration by AAV/E6/Neo in DC.

Chromosomal integration of the AAV/E6/Neo genome was undertaken by vector-chromosome junction PCR amplification and Southern blot analysis as previously described (Liu. Y., et al., J. Inf. Cytok. Res. 2000; 20:21–30). Chromosomal integration of the AAV/E6/Neo vector in DC was observed. Chromosomal integration, while not essential for gene expression from AAV vectors, does signifies a permanent genetic alteration of the DC, and is a desirable "gold standard" for viral transduction. Chromosomal integration was demonstrated by PCR amplification of vector-chromosome junctions using primers complementary to the SV40 promoter within the vector and Alu I repetitive chromosomal elements. DC were similarly treated as in the RNA analysis experiments of FIG. 9. Junction products were analyzed by agarose gel electrophoresis, Southern blotted, and probed for Neo sequences. Briefly, total cellular DNA from the infected, CD83+ selected cells and uninfected cells served as template in PCR amplification assays using primers targeting the SV40 early promoter of the vector and the cellular repetitive Alu I element. The products were Southern blotted and probed with $^{32}$P-Neo DNA, shown in FIG. 11. The positive control lane contained 100 ng of Eco RV digested AAV/GM-CSF/Neo plasmid (6.7 & 1.3 Kb). The negative control lane contained products from a PCR reaction with DNA mock infected cells. Note that multiple Neo-positive bands result from the infected DC population indicating chromosomal integration by the vector, and that multiple vector-positive cell clones are present in the population. As shown in FIG. 11, multiple vector-chromosomal junction products were observed in the AAV/E6/Neo infected DC, but not in mock infected DC. Unfortunately, the vector must integrate close to an Alu I element in order to be identified by this technique. In any case, these data indicate that at least some of the viral genomes are able to chromosomally integrate in the DC population.

Chromium Release Assay of CTL Activity

Non-adherent PBMCs (T cells and B cells) were washed and resuspended in AIM-V at 10–20×10$^6$ cells/well in 6-well culture plates (Costar, Cambridge, Mass.) with rAAV or GST-E6 pulsed DC (ratios from 20:1, responders:dendritic). The cultures were supplemented with recombinant human GM-CSF (500 U/ml) and recombinant human IL-2 (10 U/ml). At 7 days post-addition of the PBMC, the cells were assayed for tumor cell killing activity in a 6-hour chromium-51 release assay as previously described (Santin, A. D., et al., J. Virol., 1999: 73: 5402–5410). One of two HLA class I A1 compatible primary cervical tumor cells was $^{51}$Cr-labeled and used as targets as previously described (Santin, A. D., et al., J. Virol., 1999: 73: 5402–5410). To determine the structures on the target cells involved in lysis, monoclonal anti-Class I Mabs were used to block cytotoxicity. The $^{51}$Cr-labeled tumor targets were pre-incubated with Mabs specific for monomorphic HLA class I W6/32 (50 ug/ml) (hybridoma obtained from the ATCC, Rockville, Md.). The effector cells and $^{51}$Cr-labeled targets were then incubated in a final volume of 200 ul for 6 hours at 37° C. with 5% $CO_2$.

Cell Surface Marker Analysis of T cells and DC by Flourescent Antibody Cell Sorting (FACS)

For the analysis of T cells, at day 12 of the experiment the primed T cell populations were analyzed for surface markers. A panel of mAbs recognizing the following antigens was used: anti-CD4, anti-CD8, anti-CD56 (Pharmingen, San Diego, Calif.). Control irrelevant isotype-matched FITC- or PE-conjugated mAbs were obtained from Becton-Dickinson. These cells were greater than 95% viable as assessed by trypan blue exclusion. Cell suspensions were counted and distributed into 12×75 mm tubes. Mouse monoclonal antibodies were diluted in cold assay buffer and the final pellet was resuspended in 500-µl volume. Tubes were incubated for 30 minutes followed by two washes with assay buffer and the final cell pellet was resuspended in 500 µls of assay buffer for subsequent analysis. Cells were analyzed with a fluorescence activated cell sorter (FACS; Becton-Dickinson) with a 15 mW argon laser with an excitation of 488 nm. Fluorescent signals were gated on the basis of cell dimension (i.e. forward and right angle light scattering typical of PBL activated. Gated signals (5,000–10,000) were detected at 585 BP filter and analyzed using Cell Quest software (Becton-Dickinson).

For the analysis of DC, a panel of mAbs recognizing the following antigens was used: anti-CD40 (Immunotech, Marseille, France); anti-CD14, anti-DR, anti-CD80 (Becton-Dickinson), anti-CD86 (Pharmingen, San Diego, Calif., USA), anti-CD83 (Coulter, Miami, Fla., USA). Control irrelevant isotype-matched FITC- or PE-conjugated mAb were obtained from Becton-Dickinson. Briefly, non-adherent cells were harvested by washing the plates with phosphate buffered saline (PBS pH 7.2, Gibco). Adherent cells were recovered by incubating the plates at room temperature for 15–20 minutes in the presence of Cal+ and Mg'+−free PBS, followed by gentle scraping. These cells were>95% viable as assessed by trypan blue exclusion. Cell suspensions were counted and distributed into 12×75 mm tubes. Mouse monoclonal antibodies were diluted in cold assay buffer (PBS, pH 7.2, supplemented with 0.I % FBS) and added in a 50 µl volume. For direct fluorescence, tubes were incubated for 30 min followed by two washes with assay buffer and the final cell pellet was resuspended in 500 µl assay buffer for subsequent analysis.

AAV-Mediated Pulsing of DC Results in Rapid and Effective T Cell Priming

With strong evidence of DC transduction and expression by the AAV/E6/Neo vector, the ability of the AAV/E6/Neo vector to antigenically pulse DCs was analyzed. Adherent Mo were mock, GST-E6, or AAV/E6/Neo virus pulsed as before (FIG. 8D). Each of these cultures were then treated with GM-CSF and IL-4 as prescribed by Sallusto and Lanzavecchia (1994) and Romani et al. (1994) for generating DC. At day 5 the resulting DCs were then incubated with non-adherent peripheral blood lymphocytes. At day two of IL-4 treatment, representative pictures were taken of the cultures at low and high power. Note that the virus treated DC-T cell cultures exhibited much higher levels of rosetted cell clusters, suggesting stronger DC-T cell interaction.

Figure 12A:
FIG. 12 shows the early appearance of priming rosettes during AAV-mediated priming.
Figure 12B:
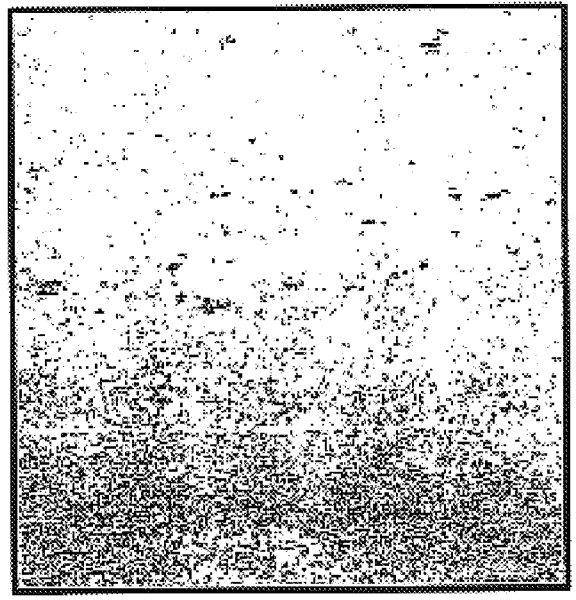
Figure 12C:
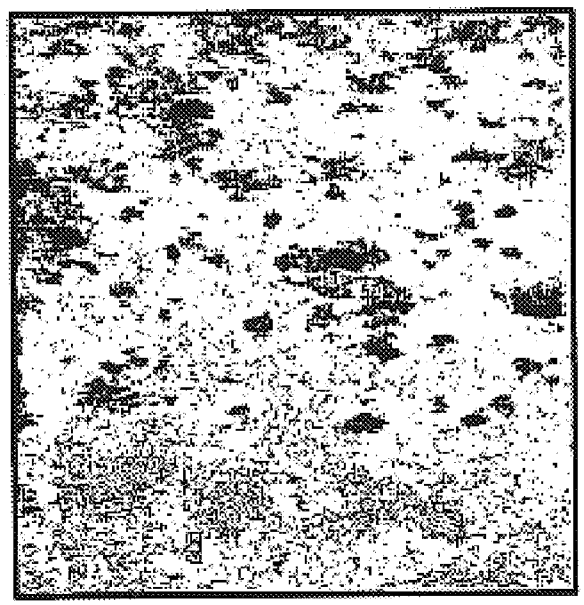

As AAV/antigen pulsing is novel, the cultures were observed on a daily basis. It was almost immediately noticed that cell clustering was taking place in an enhanced manner in the AAV-pulsed DC cultures relative to the protein-pulsed or lysate control cultures (FIG. 12). Upon examining the cell morphology present, the present inventors believe these clusters to be due to T cell-DC resetting. This led to the speculation by the inventors that the AAV-pulsing of DC might be allowing for more rapid priming of the T cells. After 7 days of priming the rosettes were dispersing. This change was interpreted as signaling the completion of priming and the subsequent death of the DC as a target. This is in sharp contrast to the protein- and lysate pulsed cultures which still did not show extensive resetting. Normally DC-T cell incubation and priming require 2 to 3 weeks to allow for significant cytotoxic T lymphocyte activity (CTL). AAV-pulsing of DCs may require only 7 days of priming.

Figure 13A:
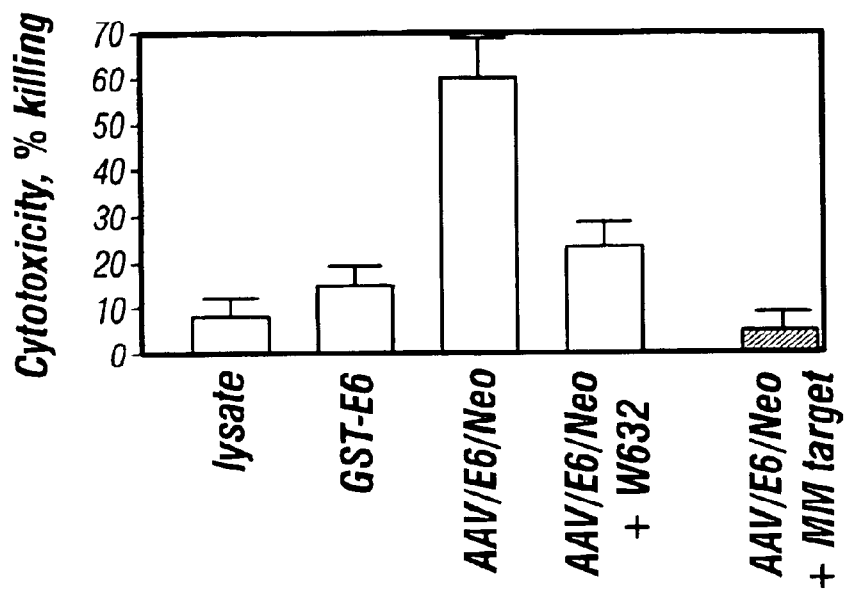
FIG. 13 shows the cytotoxic response resulting from AAV vector and DOTAP-protein lipofection after 7 days of priming.
Figure 13B:
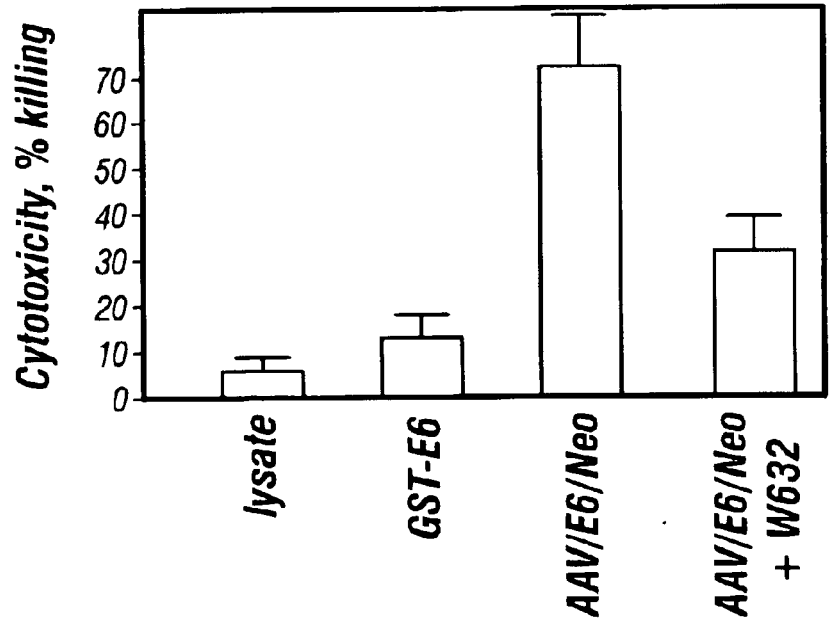

The ability of these 7 day-primed T cells to carry out class I restricted recognition and killing of HLA A1 matched primary cervical cancer cells was tested in chromium release assays. The previously characterized primary cervical cancer cell line 1, CA-1, was used as a target. Our impressions of rapid priming was fully borne out by the level of target killing. A representative experiment is shown in FIG. 13. FIG. 13A Shows a representative experiment of cytotoxic response resulting from the indicated pulsing techniques Mo/DC, and T cells from a normal individual against HLA A1 matched primary cervical cancer cells (CA1) and a primary multiple myeloma (MM). Note that the addition of the class I blocking antibody W632 greatly inhibits killing. Also note lack of killing activity against the primary MM. FIG. 13B shows a representative experiment of cytotoxic response against a second HLA A1 matched primary cervical cancer (CA2). Again, note that the addition of the class I blocking antibody W632 greatly inhibits killing.

Normally, protein/DOTAP pulsing of DC results in significant target killing. However, by allowing only a short period of priming, the percent killing resulting from this technique was only slightly above the cell lysate control (mock). In sharp contrast, the AAV/E6/Neo-pulsed-DC-primed T cells resulted in much higher killing activity than the protein primed and lysate controls. These same AAV/E6/Neo primed cells were unable to lysis an unrelated multiple myeloma target. Finally, the addition of the anti-class I antibody W632 significantly blocked killing, indicating class I restriction of killing. We next assayed for class I restricted killing of a second HLA A1 matched, previously characterized primary cervical cancer cell line CA-2 (Santin, A. D., et al., J. Virol. 1999; 73: 5402–5410). The resulting killing was very similar to that against CA-1 (FIG. 13). Again, the addition of the anti-class I antibody W632 significantly blocked killing, indicating class I restriction of killing. Finally, because non-purified virus was utilized in these experiments which contained lysed cellular components, the CTL experiment was repeated using a heparin column-purified virus stock. DC were pulsed with $10^7$ purified encapsidated genomes of AAV/E6/Neo (approximately $10^{-3}$ virus used in the FIG. 13 experiments). A CTL assay was then carried out on the CA1 cervical cancer primary target as described in FIG. 13. The resulting killing for AAV/E6/Neo, AAV/E6/Neo plus anti-class I antibodies, GST-E6, and lysate control pulsing of DC was 36.1+/−1.4%, 0.4+/−0.3%, 3.1+/−1.4%, and 2.0+/−0.5%, respectively. These data indicate that the CTL activity in all of these experiments was in fact due to AAV/E6/Neo viral transduction/pulsing of DC.

Example 3
Higher CD8/CD4 and Lower CD56/CD8 Cell Ratios result with AAV-Mediated Pulsing/Priming The makeup of the T cell populations, which resulted from AAV-transduction or protein lipofection, was observed. An effective CTL response, while requiring CD8+ T cells as an effector of lysis, also requires CD4+ helper T cells. Flow cytometric analysis was used to determine the phenotype of the population of the lysate, GST-E6 pulsed, and AAV/E6/Neo pulsed T cell populations.

Figures 1, 2, 3, 4, 14A:
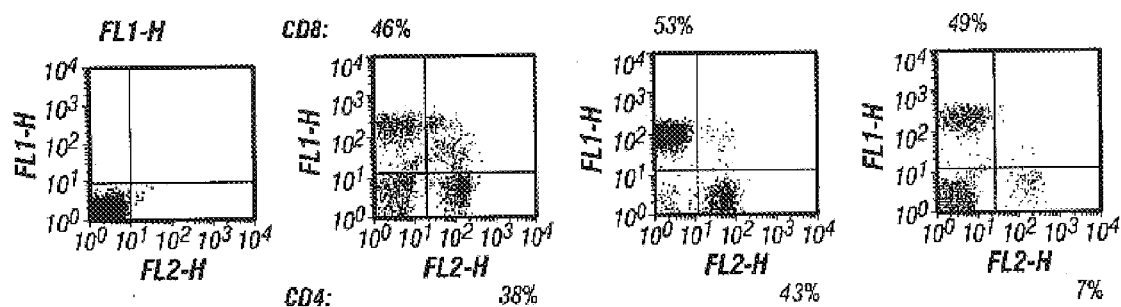
Figures 1, 2, 3, 4, 14B:
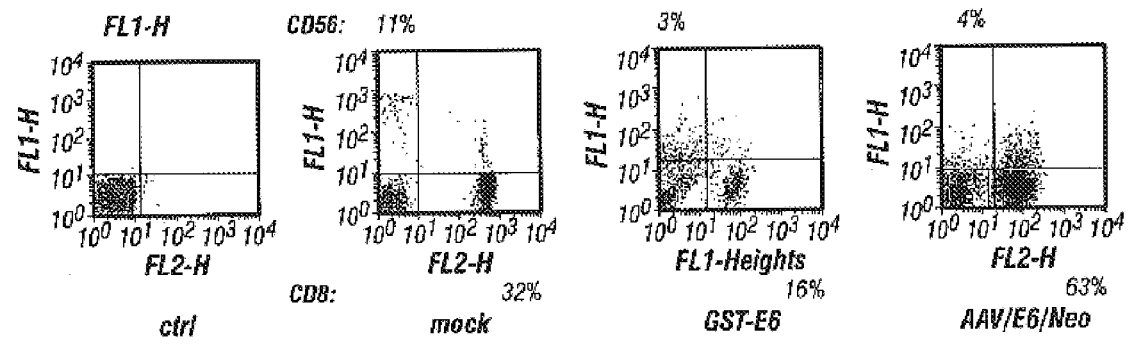

FIG. 14A shows the CD8 and CD4 prevalence within the primed population resulting from three different techniques as indicated (on the right), as well as an FL1-H, FL2-H control (left). FIG. 14B shows the CD56 and CD8 ratios in the same experimental situations as A.

As shown in FIG. 14A, in the mock case, one sees a normal ratio of CD8 to CD4 postive cells (1.21:1). In the GST-E6 pulsing case, the D8/CD4 ratio remains the same (1.23:1). In sharp contrast in the AAV/E6/Neo pulsed case, the ratio of CD8/CD4 changes dramatically to 7.0:1. Normally, one would not expect this high ratio to arise until three weeks of DC/T cell priming suggesting that the AAV-Ag pulsing of DC results in not only quicker activation, but also higher killing activity, HLA class I restricted, on a per CD8+ T cell basis. The high killing is consistent with a Type 1 (Th 1) response. This is important because recent studies have suggested that progression to cervical cancer from precursor lesions may be associated with a preferential Type 2 (Th 2) T cell response, along with significant dysfunction of Type 1 T cell response in patients with high grade cervical intraepithelial lesions and invasive cervical cancer (Cleric M., et al., J. Natl. Can. Inst. 1997; 90: 261-3).

The expression of CD56 was also observed. Some consider this marker as being specific for natural killer T cells. However, others have reported that some CD8+ T cells do express CD56 and do exhibit HLA class I restricted killing. In spite of this confusion, all of T cell populations tested herein exhibited low CD56 expression. However, what is noteworthy in this analysis is the very high level of CD8+ T cells in the case of AAV/E6/Neo pulsing, confirming the CD8/CD4 analysis (FIG. 14A). Taken together, these data indicate a very different resulting primed T cell population when AAV-antigen pulsing was used, and suggests that the increased killing activity may be a result of these changes in the T cell population These data also indicate that CD8 is a specific lineage marker in HLA class I restriction in our system.

Figures 1, 16A:
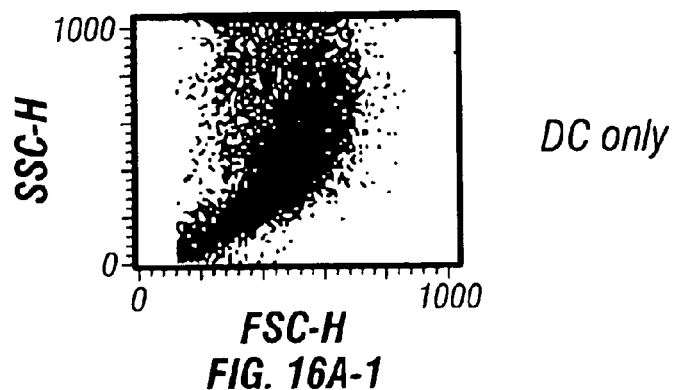
Figures 2, 16A:
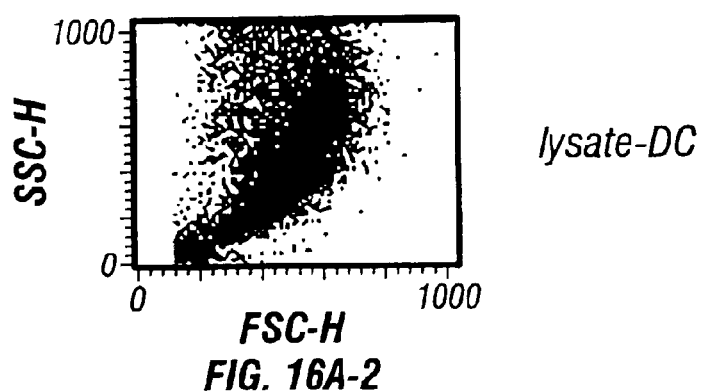
Figures 3, 16A:
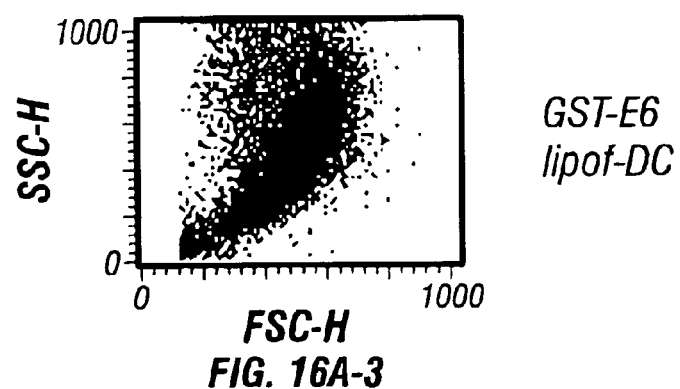
Figures 4, 16A:
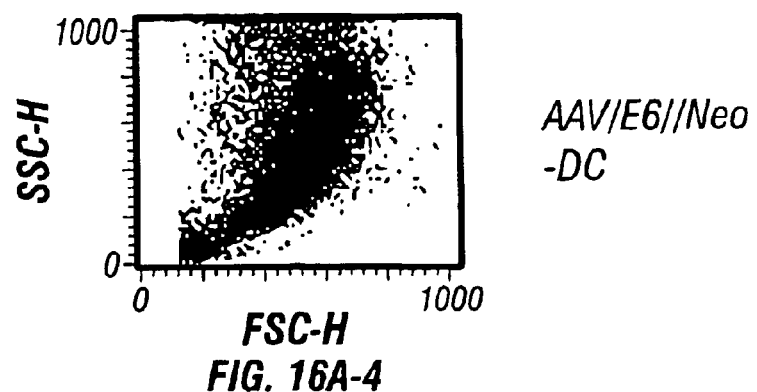
Figures 1, 16B:
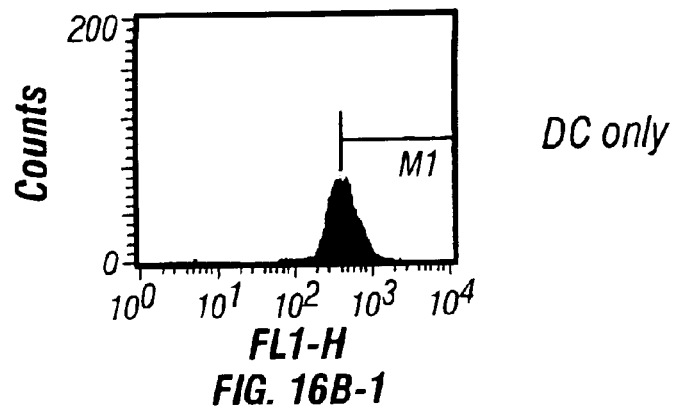
Figures 2, 16B:
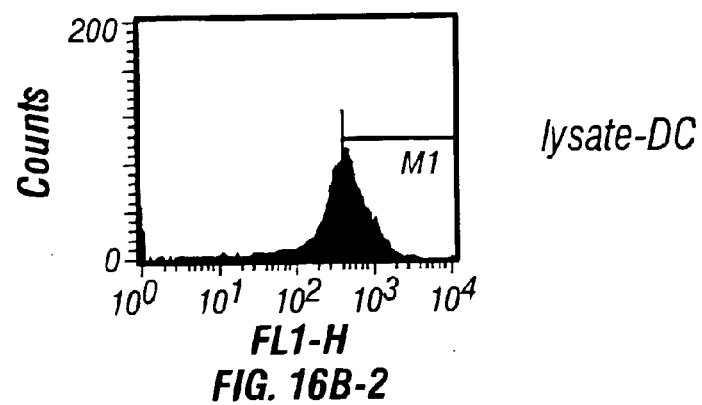
Figures 3, 16B:
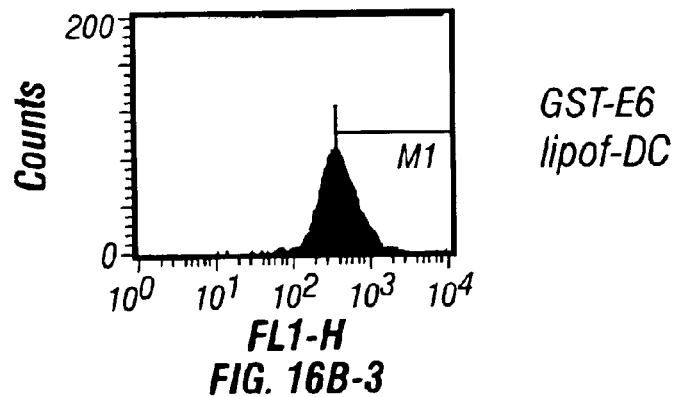
Figures 4, 16B:
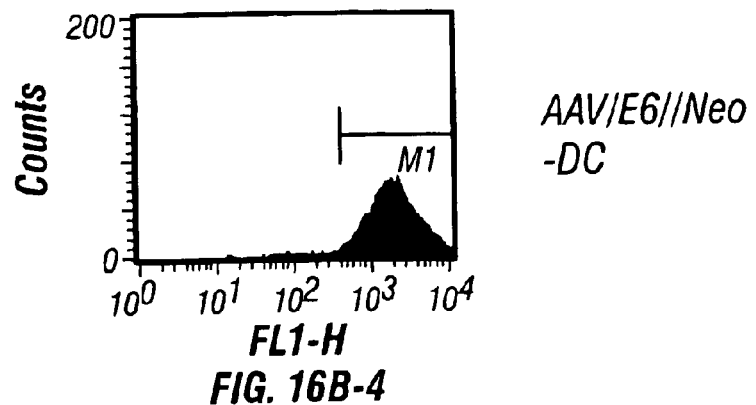

Example 4
AAV/E6 Vector-Pulsing Results in DC with Higher CD80, and Lower CD86 Expression Finally, the DC resulting from the various pulsing techniques was characterized to observe if significant differences were discernable. Flow cytometric analysis was used to determine the phenotype of untreated, lysate-pulsed, GST-E6-pulsed, and AAV/E6/Neo-pulsed DC populations. The results, shown in FIGS. 15 and 16, demonstrate that the DC generated from all for techniques share all of the common DC markers. However, AAV/E6/Neo pulsed DC did express significantly higher levels of CD80 and lower levels of CD86 than the GST-E6-pulsed DC. In FIG. 15, Mo were treated as indicated, treated with GM-CSF and IL-4 and analyzed by FACS for mean flourescent intensity (MFI) on day 7. "−" no detectable MFI staining, "+"=MFI $10^1$–$10^2$. "++"=MFI $10^2$–$10^3$. "+++"=MFI $10^3$–$10^4$. Representative of three experiments. Note AAV-pulsing results in higher CD80 and lower CD86 levels compared to protein pulsing. FIG. 16 provides histograms of CD80 expression complied in FIG. 13. FIG. 16A provides the size analysis of general DC populations, and FIG. 16B provides the DC CD80 expression under different conditions.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which this invention pertains.

We claim:

1. A method of screening a patient for breast cancer, the method comprising:
   a) assaying for the presence of human papillomavirus in a sample from a biopsy taken from a patient,
   wherein said assaying comprises amplifying human papillomavirus gene sequences by use of a pair of primers to produce an amplified product, and probing said amplified product for the presence of HPV 16 and a second human papillomavirus selected from the group consisting of HPV18, HPV31, HPV33, HPV35, HPV45, HPV58,
   wherein said pair of primers is SEQ ID NO: 1 and SEQ ID NO: 2, and
   wherein presence of HPV 16 and said second human papillomavirus is indicative of breast cancer in said patient.

2. The method of claim 1 wherein the patient is a human, wherein the cancer is in any stage of development.

3. The method of claim 1 wherein the biopsy is obtained by performing the technique of ductal lavage on a breast of a patient.

4. The method of claim 1 wherein said amplifying is achieved by use of polymerase chain reaction amplification.

5. The method of claim 1 wherein said amplifying is achieved by use of reverse-transcription polymerase chain reaction amplification.

* * * * *